US011385340B2

(12) United States Patent
Kook et al.

(10) Patent No.: US 11,385,340 B2
(45) Date of Patent: *Jul. 12, 2022

(54) ULTRASOUND IMAGING SYSTEM INCLUDING WIRELESS PROBE TRACKING

(71) Applicant: FUJIFILM SONOSITE, INC., Bothell, WA (US)

(72) Inventors: John Kook, Seattle, WA (US); Jon Battershell, Bothell, WA (US); Jason Nguyen, Bothell, WA (US)

(73) Assignee: FUJIFILM SONOSITE, INC., Bothell, WA (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/071,813

(22) Filed: Oct. 15, 2020

(65) Prior Publication Data

US 2021/0063554 A1 Mar. 4, 2021

Related U.S. Application Data

(63) Continuation of application No. 16/011,400, filed on Jun. 18, 2018, now Pat. No. 10,838,050.

(51) Int. Cl.
*G01S 7/52* (2006.01)
*A61B 8/00* (2006.01)
*A61B 6/00* (2006.01)

(52) U.S. Cl.
CPC ........ *G01S 7/52098* (2013.01); *A61B 6/4411* (2013.01); *A61B 8/4433* (2013.01); *A61B 8/461* (2013.01); *A61B 8/565* (2013.01); *G01S 7/52053* (2013.01); *G01S 7/52085* (2013.01)

(58) Field of Classification Search
CPC ............ G01S 7/52098; G01S 7/52085; G01S 7/52053; G01S 7/52082; A61B 6/4411; A61B 8/461; A61B 8/565; A61B 8/4433; A61B 8/4477; A61B 8/4438; A61B 8/4427; A61B 8/4254; A61B 8/4472
See application file for complete search history.

(56) References Cited

U.S. PATENT DOCUMENTS

| 10,838,050 | B2* | 11/2020 | Kook ................ A61B 8/4433 |
| 2013/0158397 | A1 | 6/2013 | K. et al. |
| 2015/0002606 | A1 | 1/2015 | Hyde et al. |
| 2019/0142379 | A1 | 5/2019 | Schmedling |
| 2019/0383920 | A1* | 12/2019 | Kook ................ A61B 8/4427 |
| 2021/0063554 | A1* | 3/2021 | Kook ................ A61B 8/4477 |

* cited by examiner

*Primary Examiner* — Daniel Pihulic
(74) *Attorney, Agent, or Firm* — Womble Bond Dickinson (US) LLP (57) ABSTRACT

Ultrasound imaging systems including transducer probes having wireless tags, and associated systems and methods, are described herein. For example, the wireless tags can store supplemental data about the transducer probes, and the ultrasound system can include a base unit configured to wirelessly communicate with nearby ones of the wireless tags to receive the supplemental data. The base unit can be further configured to display the transducer probes that are nearby. In some embodiments, the operator can filter or sort the displayed nearby transducer probes based on the supplemental data to identify a particular one of the nearby transducer devices that has one or more desired attributes.

20 Claims, 3 Drawing Sheets

ULTRASOUND IMAGING SYSTEM INCLUDING WIRELESS PROBE TRACKING

The present application is a continuation of U.S. patent application Ser. No. 16/011,400, titled "ULTRASOUND IMAGING SYSTEM INCLUDING WIRELESS PROBE TRACKING", filed on Jun. 18, 2018 and which is incorporated herein by reference in its entirety.

TECHNICAL FIELD

The present technology relates to ultrasound imaging systems, and in particular to systems including transducer probes having wireless tags for improving workflow within clinical settings.

BACKGROUND

In ultrasound imaging, an operator of an ultrasound system uses a probe to obtain data for ultrasound images of a patient during an imaging procedure. Multiple probes may be compatible with the same system, and a particular probe or probes may be more suitable for a certain imaging procedure than other probes. Often, the operator is unaware that a more suitable probe for the imaging procedure is nearby (e.g., in the same room as the ultrasound system). Alternatively, the operator may be aware of nearby probes that are available for use during the imaging procedure, but unaware that a certain probe is more suitable for the procedure than a probe they have selected for use during the imaging procedure.

DETAILED DESCRIPTION

Specific details of several embodiments of ultrasound systems having wireless communication between a base unit and one or more probes are described below. In some embodiments, for example, an ultrasound imaging system includes a plurality of transducer devices each having a wireless tag storing data about the transducer device. The ultrasound system further includes a base unit including a display, a memory storing instructions, and a processor or logic circuitry. The processor or logic circuitry can be configured to receive data from one or more of the wireless tags about nearby transducer devices located proximate to the base unit. The processor or logic circuitry can further be configured to produce a graphic on the display or other cue alerting a user of the device(s) that are located proximate to the base unit. In some embodiments, the graphic is a list that the operator may sort or filter based on the data from the wireless tags in order to identify a particular one of the nearby transducer devices that has a desired attribute.

Certain details are set forth in the following description and in FIGS. 1-3 to provide a thorough understanding of various embodiments of the present technology. In other instances, well-known components, devices, structures, materials, operations, and/or systems often associated with ultrasound imaging systems are not shown or described in detail in the following disclosure to avoid unnecessarily obscuring the description of the various embodiments of the present technology. Those of ordinary skill in the art will recognize, however, that the present technology can be practiced without one or more of the details set forth herein, or with other structures, methods, components, and so forth. The phrases "in some embodiments," "according to some embodiments," "in certain embodiments," "in the illustrated embodiment," "in other embodiments," and the like generally mean the particular feature, structure, or characteristic following the phrase is included in at least one implementation of the present technology, and may be included in more than one implementation. In addition, such phrases do not necessarily refer to the same embodiments or different embodiments.

The terminology used below is to be interpreted in its broadest reasonable manner, even though it is being used in conjunction with a detailed description of certain examples of embodiments of the technology. Indeed, certain terms may even be emphasized below; however, any terminology intended to be interpreted in any restricted manner will be overtly and specifically defined as such in this Detailed Description section.

I. Selected Embodiments of Ultrasound Systems Having Wireless Tags

Figure 1:
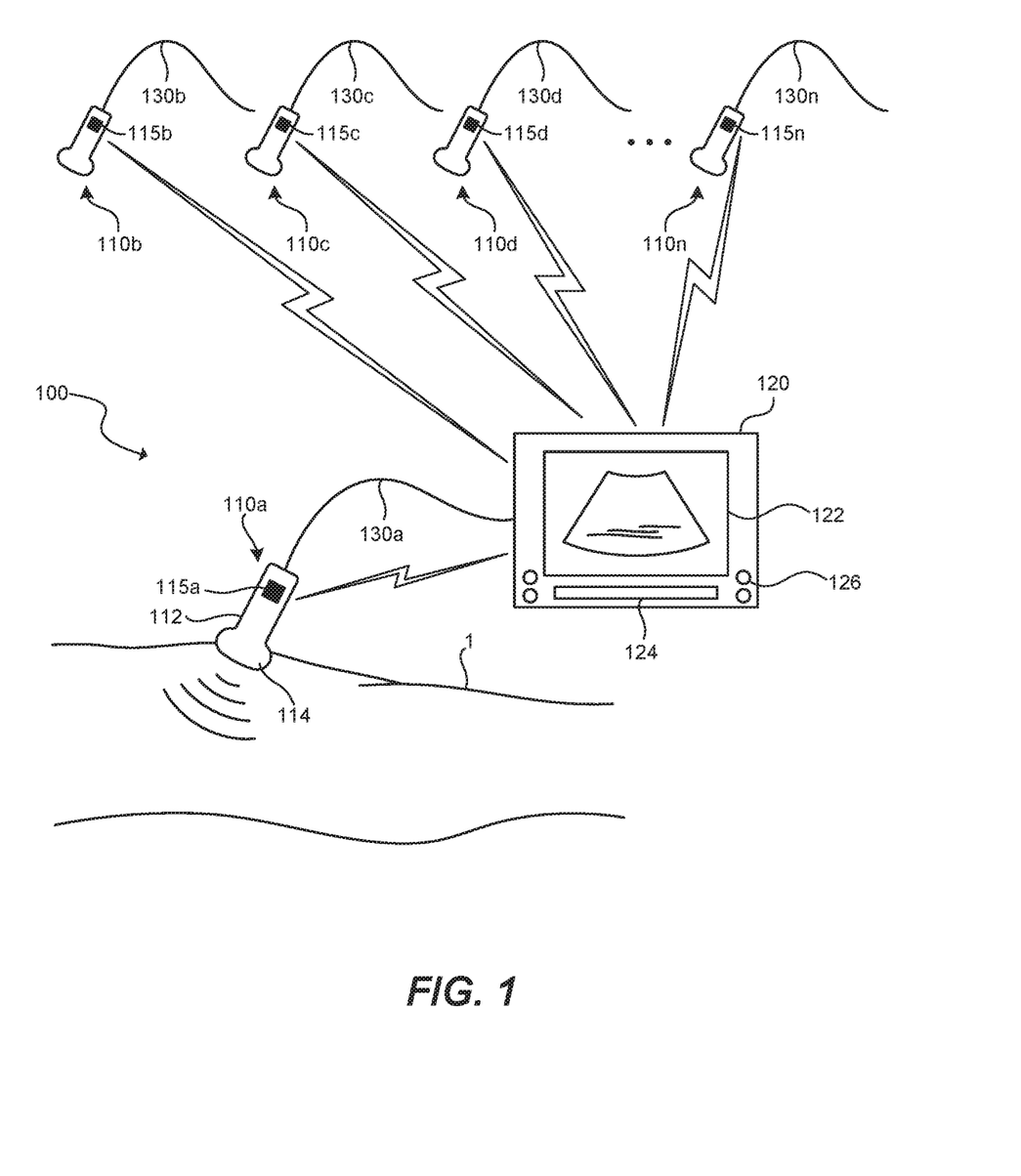
FIG. 1 is a simplified illustration of an ultrasound imaging system configured in accordance with an embodiment of the present technology.

FIG. 1 is a partial schematic illustration of an ultrasound imaging system 100 ("system 100") for imaging a region of interest of a subject or patient 1. In the illustrated embodiment, the system 100 includes an ultrasound transducer device or probe 110*a* ("probe 110*a*") operably coupled to a base unit 120 by a signal cable 130*a*. The probe 110*a* includes a housing 112 (e.g., a molded plastic housing) having a scan head region 114 that encloses a single movable transducer element or an array of transducer elements. In some embodiments, the probe 110*a* can include one or more buttons, triggers, touch sensors, or other input devices (not shown) configured, for example, to toggle power on or off, to put the system 100 in a run/standby state, or to perform other operations. The base unit 120 can be a hand-held, portable, or cart-based unit including a display 122 (e.g., a touchscreen display), one or more operator controls 124, and input/output ports (I/O) 126. The operator controls 124 can include, for example, buttons, knobs, switches, a keyboard, a touchscreen, etc. The I/O ports 126 can include, for example, audio, universal serial bus (USB), high-definition multimedia interface (HDMI) ports), EKG ports, etc.

During an ultrasound imaging procedure, an operator (e.g., a physician, sonographer, ultrasound technician, etc.) can use the probe 110*a* and the base unit 120 to perform an ultrasound scan. In particular, the operator can direct the probe 110*a* toward the region of interest (e.g., an organ, a vessel, an internal cavity, etc.) of the patient 1 and use the probe 110*a* to transmit ultrasound signals into the region of interest and to receive the corresponding echo signals. The system 100 converts one or more characteristics of the received echo signals (e.g. their amplitude, phase, power, frequency shift, etc.) into image data that is formatted and displayed for the operator as an image on the display 122. In some embodiments, the operator can use the operator controls 124 to input information about the particular region of interest, characteristics of the patient 1, or other information relevant to the imaging procedure into the system 100.

In some embodiments, the system 100 can include more than one probe that is compatible with the base unit 120 and that can be operably connected to the base unit 120 for performing an ultrasound scan. For example, in addition to the probe 110a, the system can include a plurality of probes 110b-110n (collectively "probes 110"). Each of the probes 110 can have generally similar features or components (e.g., a housing enclosing one or more transducer elements configured to transmit ultrasound signals), but can have different form factors, operating frequencies, focal depths, and/or other characteristics that are optimized for different imaging functions. Accordingly, as described in detail below, depending on the particular imaging procedure to be carried out on the patient 1, a particular one or ones of the probes 110 may be more appropriate (e.g., better suited, customized, adapted, etc.) for the imaging procedure than the others. In the illustrated embodiment, each of the probes 110 includes a corresponding signal cable 130 (labeled individually as signal cables 130b-130n) for operably coupling the probes 110 to the base unit 120. In other embodiments, the probes 110 can be configured for wireless communication and operation with the base unit 120. In some embodiments, the base unit 120 can be operably connected to more than one of the probes 110 at the same time.

As further illustrated in FIG. 1, each of the probes 110 includes a wireless tag 115 (labeled individually as wireless tags 115a-115n). In some embodiments, the wireless tags 115 are active or passive radio-frequency identification (RFID) tags such as, for example, Bluetooth Low Energy (BLE) tags. As described in detail below with reference to FIG. 2, the base unit 120 is configured for wireless communication with the wireless tags 115 to, for example, determine that some or all of the probes 110 are located proximate to the base unit 120 and/or to receive supplemental data (e.g., supplemental information) about the probes 110. In the illustrated embodiment, the wireless tags 115 are shown affixed to the exterior of the housing of the probes 110. In other embodiments, the wireless tags 115 can be integrated with or embedded within the probes 110, or the signal cables 130 that connect the probes 110 to the base unit 120.

Figure 2:
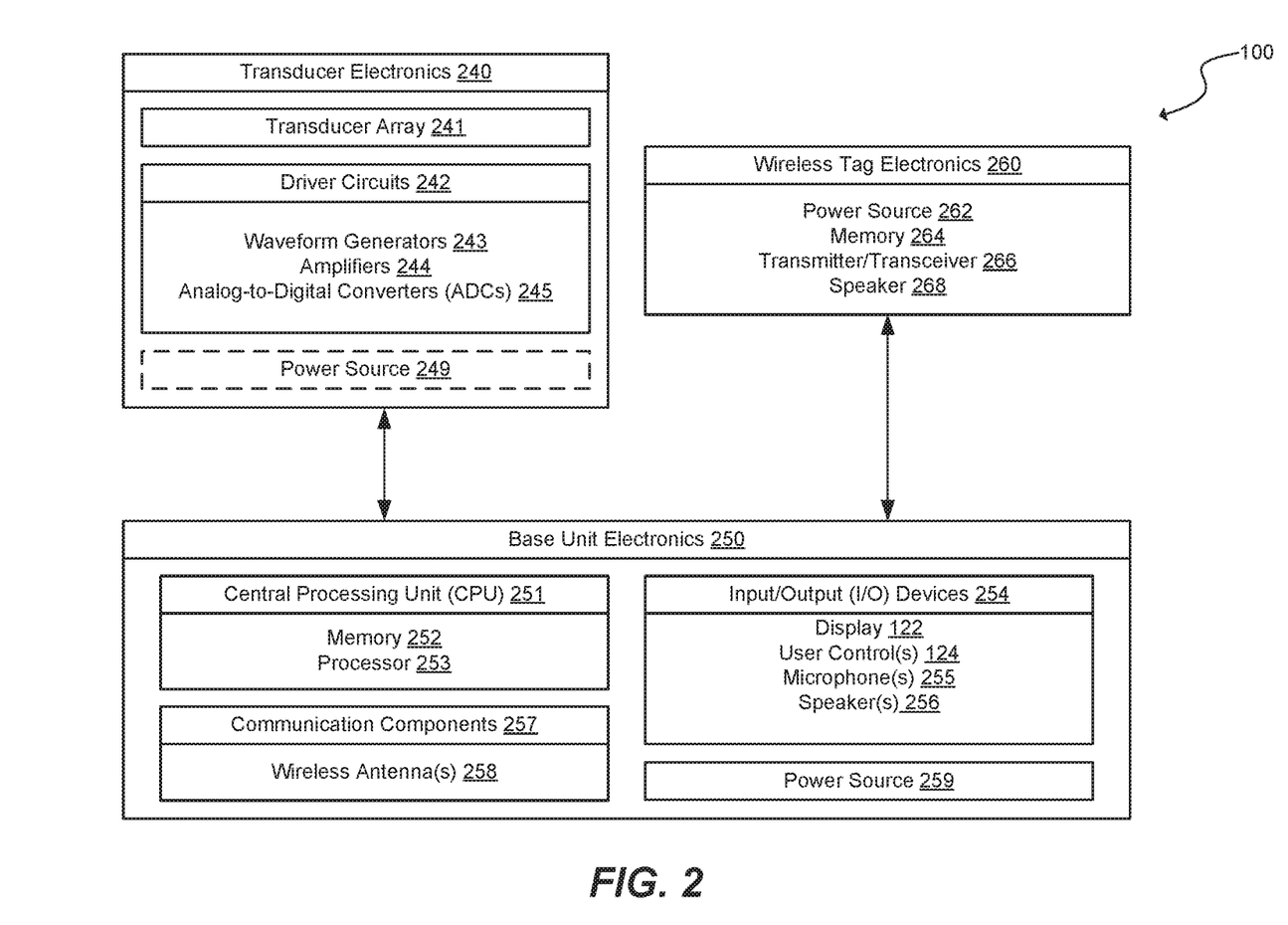
FIG. 2 is a schematic diagram of various electronic components of the ultrasound imaging system shown in FIG. 1 configured in accordance with an embodiment of the present technology.
Figure 3:
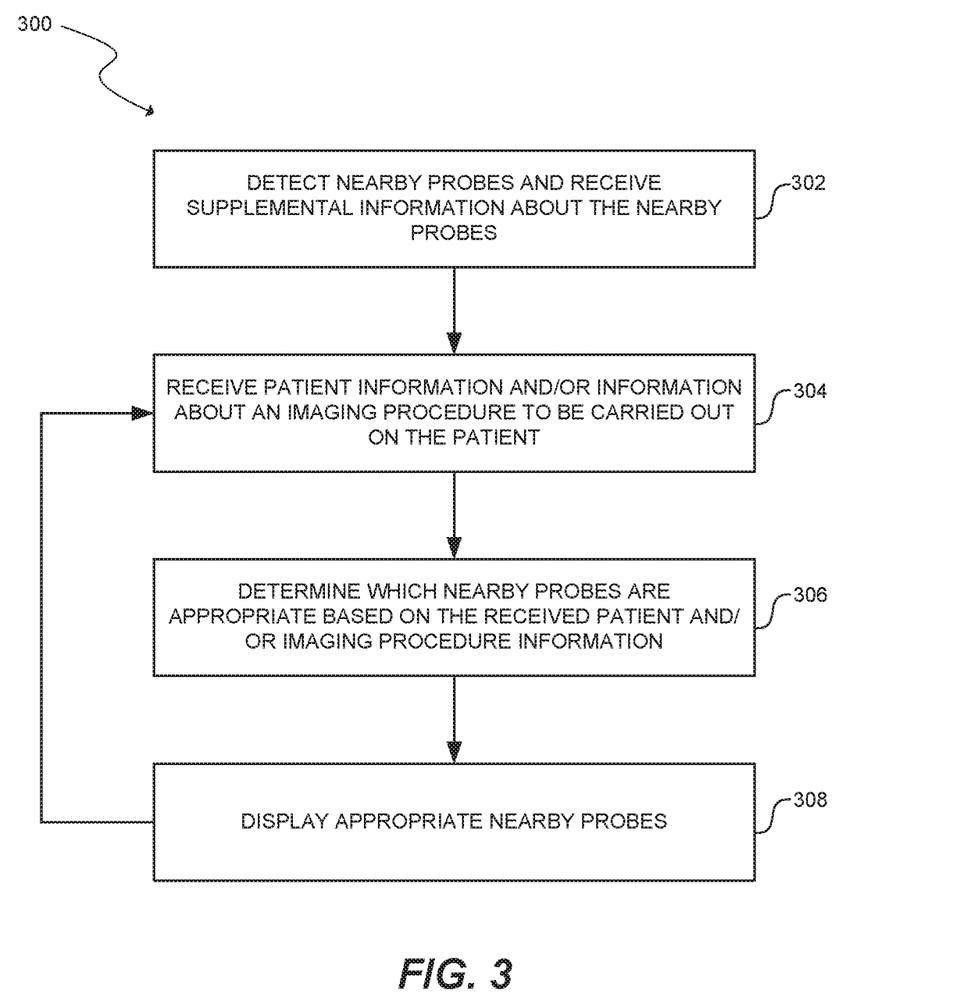
FIG. 3 is a flow diagram of a method or process of locating or selecting a nearby transducer device for an ultrasound imaging procedure in accordance with an embodiment of the present technology.

FIG. 2 is a schematic diagram of various electronic components of the system 100 shown in FIG. 1 configured in accordance with an embodiment of the present technology. In the illustrated embodiment, the system 100 includes transducer electronics 240 at each of the probes 110, base unit electronics 250 at the base unit 120, and wireless tag electronics 260 at each of the wireless tags 115. In the following description, reference is made to the probe 110a and wireless tag 115a shown in FIG. 1 for the sake of clarity.

The transducer electronics 240 can drive a transducer array 241, such as an array of piezoelectric transducer elements, located at the scan head region 114 of the probe 110a. The transducer electronics 240 can also include one or more driver circuits 242 configured to supply driving voltage to the piezoelectric transducer elements in such a fashion that an ultrasound beam is produced in a desired direction. The transducer electronics 240 can also include, for example, waveform generators 243, amplifiers 244, analog-to-digital converters (ADCs) 245, and other ultrasound signal processing components (e.g., a CPU, controller, transmit/receive beam forming circuitry, etc.). In some embodiments, at least a portion of the transducer electronics 240 can be located at the base unit 120. In some embodiments, for example where the probe 110a is configured for wireless operation with the base unit 120 without the signal cable 130a, the transducer electronics 240 can further include a power source 249 (e.g., a battery).

The base unit electronics 250 include a central-processing unit ("CPU") 251, input/out devices (I/O) devices 254, communication components 257, and a power source 259. The CPU 251 includes a programmable processor (microprocessor, GPU, DSP or equivalent logic circuits, or a combination thereof) 253 configured to execute instructions stored in a memory 252 or operate as configured in order to perform various processes, logic flows, and routines. The I/O devices 254 can include, for example, the display 122, the operator controls 124, one or more microphones 255, one or more speakers 256, USB ports, EKG ports, HDMI ports, and/or other suitable components. The communication components 257 can include, for example, signal buses coupled to the I/O ports 126, a suitable network adaptor, a wireless transceiver (e.g., Bluetooth, Wi-Fi or cellular transceiver), or other suitable components for communication over computer communication links (LAN, WAN, Internet etc.) through a wired (e.g., Ethernet, USB, Thunderbolt, Firewire, or the like) or wireless (e.g., 802.11, cellular, satellite, Bluetooth, or the like) communication link. As further illustrated in FIG. 2, the communication components 257 include one or more wireless antennas 258 for receiving/transmitting wireless signals from/to the wireless tags 115 in one or more of the probes 110. In a particular embodiment, the wireless antennas 258 are configured for communication with the wireless tags 115 via a Bluetooth connection.

In the illustrated embodiment, the wireless tag electronics 260 are not powered by the same power source that powers (e.g., are separate from) the transducer electronics 240. Accordingly, the wireless tag 115a can include a separate power source 262. In some embodiments, the power source 262 is a CR2032 lithium coin battery or other suitable battery. In other embodiments, the wireless tag electronics 260 can be at least partially coupled to or integrated with the transducer electronics 240 (e.g., sharing a common power source). As shown, the wireless tag electronics 260 further include a memory 264, and a transceiver 266 configured for wireless communication with the base unit electronics 250 via a BLE or other suitable connection. In some embodiments, the wireless tag electronics 260 further include a speaker 268 or other output device, and/or a GPS receiver or other location detection receiver.

The memory 264 can be a read-only non-volatile memory storing supplemental data about the probe 110a. For example, the data stored in the memory 264 can include information about invariable or semi-invariable properties or attributes of the probe 110a, such as its physical, operational, or functional characteristics (e.g., a center frequency, a shape (e.g., curved or linear), etc.), procedures generally performed with the probe (e.g., cardiac, abdominal, musculoskeletal, etc.), a type of patient the probe is generally used with (e.g., adult, pediatric, infant, etc.), serial numbers, warranty information, ownership information, usage information, etc. In some embodiments, the memory 264 can be a programmable memory (e.g., an electrically erasable programmable read-only memory (EEPROM)) that can be erased and reprogrammed to store data about varying attributes or properties of the probe 110a. For example, the data stored in the memory 264 can include information about: a cleaning history of the probe 110a (e.g., information about the last use and/or cleaning of the probe 110a); maintenance history or a maintenance schedule of the probe 110a (e.g., information about a date and/or time when the last current leakage or other integrity test was performed on the probe 110a, a date and/or time of the next scheduled integrity test for the probe 110a, a power level of the power source 262 of the wireless tag electronics 260, a date/time when the power source 249 and/or the power source 262 were last replaced, etc.); historical usage of the probe 110a (e.g., information about when the probe 110a was last used, the user and/or usage time, non-identifying patient data such as the number and type of patients on which the probe 110a was used, ultrasound procedures the probe 110a was previously used for, whether there were transducer element failures with the probe 110a during a previous use, etc.); an assigned location or storage site of the probe 110a (e.g., information that the probe 110a is normally stored in a particular drawer, cabinet, etc., within a particular examination room); an actual or average location of the probe 110a based on one or more detected GPS or Wi-Fi signals; a preferred status of the probe 110a (e.g., that the probe 110a is preferred by a certain operator, for a particular imaging procedure, etc.); and/or other properties or attributes of the probe 110a that may be relevant to an operator of the system 100.

In operation, the wireless tag 115a can be configured to continuously, nearly-continuously, or intermittently transmit a wireless signal (e.g., a Bluetooth or BLE signal). The base unit electronics 250 are configured to determine that the probe 110a is located proximate to (e.g., located nearby to, within a predetermined range of, etc.) the base unit 120 by detecting a wireless signal from the wireless tag 115a. As described in detail below, the CPU 251 can further process the signal from the wireless tag 115a and cause one or more of the I/O devices 254 to indicate that the probe 110a is located nearby to the base unit 120. For example, the CPU 251 can cause the display 122 to display an indication, a graphic, a map, etc., showing that the probe 110a is located proximate to the base unit 120 and further showing any of the supplemental data associated with the probe 110a.

In some embodiments, where the memory 264 is a programmable memory, the CPU 251 can operate to generate and send one or more update signals to the wireless tag 115a for updating the data stored in the memory 264. For example, the base unit electronics 250 can update the data stored in the memory 264 to reflect the latest cleaning, maintenance, use, storage location, etc., of the probe 110a. More particularly, the operator of the system 100 can use the I/O devices 254 to input the updated information into the base unit electronics 250 for transmission to the wireless tag electronics 260. In some embodiments, the base unit electronics 250 can be programmed or configured to automatically update any of the data stored by the wireless tag 115a—for example, during or after an imaging procedure is performed with the probe 110a, after maintenance is performed on the probe 110a, etc.

II. Selected Embodiments of Methods for Detecting Proximate Transducer Probes

With reference to FIGS. 1 and 2, and as set forth above, the system 100 is configured to detect that one or more of the probes 110 are located proximate to the base unit 120 by detecting signals transmitted by the wireless tags 115. That is, signals from wireless tags 115 of probes 110 that are within range of the base unit 120 (e.g., in the same room in a medical facility as the base unit 120) will be detected and those probes 110 will be determined to be proximate to the base unit 120, while probes 110 that are out of range of the base unit 120 (e.g., in a different room in the medical facility) will not be detected by the base unit 120. The detection of proximate probes 110 may be automatically performed or manually initiated by the operator of the system 100.

In some embodiments, the system 100 can perform a general search to detect each of the probes 110 that are located proximate to the base unit 120. For example, an automatic search may begin once a user has specified various information about the usage of the system 100, such as exam type, patient data, or similar information. In some embodiments, the system 100 may analyze which probes 110 are currently connected to the base unit 120 to determine if alternative options are required or more well suited for the various inputted information. In other embodiments, the operator of the system 100 can initiate a search for nearby probes 110 that have specific attributes by entering information into the base unit 120 via the operator controls 124, or by selecting desired attributes of a particular imaging mode from a menu. The system 100 can then analyze the supplemental data received from the wireless tags 115 to identify the nearby probes 110 having the specified attributes. In a particular example, the operator of the system 100 could initiate a search for a probe 110 having a specific serial number. The base unit 120 can then send a request message to the wireless tag 115 associated with the probe 110 having the specific serial number and the wireless tag 115 can respond with its location. If the probe 110 cannot be detected, the operator could then walk around with or otherwise move the base unit 120 and, when the wireless tag 115 associated with the probe 110 having the specific serial number is within range, the system 100 could signal (e.g., via the display 122, the speakers 256, or another suitable output device) that the probe 110 having the specific serial number is nearby. In another example, the operator could enter a generic probe type to search for (e.g., a 5 MHz linear transducer) and the processor of the base unit 120 can transmit a request for probes 110 having the desired characteristics. If none are found, the operator can proceed to move the base unit 120 until the system 100 identifies a particular probe 110 of that type nearby.

In some embodiments, the system 100 is further configured to specifically locate the probes 110 relative to the base unit 120. In some embodiments, for example, in response to an operator selection (e.g., in response to the operator selecting one of the proximate probes 110 from a list displayed on the display 122), the base unit 120 can send an instruction to the wireless tag 115 of the selected probe 110 to produce a sound via the speaker 268. In some embodiments, the sound produced via the speaker 268 can be an audible sound (e.g., a chirp) that enables the operator to track and locate the selected probe 110. In other embodiments, the sound produced via the speaker 268 can be an inaudible sound (e.g., having a frequency of greater than about 20 kHz) that is detectable by the microphones 255 of the base unit electronics 250. In other embodiments, the base unit electronics 250 are configured to determine an approximate direction and/or to triangulate a specific position of the selected probe 110 relative to the base unit 120 based on, for example, a time difference between when the microphones 255 receive the sound from the wireless tag 115 of the selected probe 110. If the wireless tag electronics 260 include a position sensor (GPS locator), the location of the selected probe 110 can be sent to the base unit 120. The determined location or direction of the selected probe 110 can be outputted to the operator via the I/O devices 254. In some embodiments, for example, the base unit 120 can be configured to generate and display one or more directional indicators on the display 122. In certain embodiments, the directional indicators can vary in intensity based upon a determined distance from the base unit 120 to the selected probe 110.

In yet other embodiments, the base unit 120 can include multiple wireless antennas 258 each configured (e.g., shaped and positioned) to detect wireless tags 115 located within a certain sector or angle relative to the base unit 120. For example, the base unit electronics 250 could include three wireless antennas 258 each positioned to receive signals from wireless tags 115 in a different sector spanning about 120° around the base unit 120. Accordingly, based on a particular one of the wireless antennas 258 that detects the selected probe 110, the processor in the base unit 120 can determine an approximate direction or location of the selected probe 110 relative to the base unit 120. In still other embodiments, the wireless antennas 258 could partially or fully overlap (e.g., the wireless antennas 258 could each be omnidirectional). In such embodiments, the time differences between when the different wireless antennas 258 detect the wireless tag 115 of the selected probe 110 could be used to determine an approximate direction and/or a specific position of the selected probe 110 relative to the base unit 120.

In some embodiments, as described in detail above, the supplemental data stored within the wireless tags 115 includes location or storage information about the probes 110, such as a normal storage location for each of the probes 110. The normal storage locations can be average GPS positions for the probes 110, or other descriptive information about the storage location of the probes—for example, that a particular one of the probes 110 is assigned to and normally stored in a particular drawer in a particular examination room. Accordingly, in such embodiments, the base unit 120 can simply display or otherwise indicate to the operator the assigned (e.g., normal) storage location of a selected probe 110, the owner of the probe, performance capabilities, license data, and/or cost for use.

In certain embodiments, the system 100 can be configured to produce an alert (e.g., a visual or audible alert) when a probe 110 is moved out of range of the base unit 120 to reduce the likelihood of the probes 110 being lost or stolen. For example, if a periodic heart beat signal from one of the wireless tags 115 is lost (e.g., no longer detected by the base unit electronics 250) and/or below a threshold level, the system 100 can produce an audible alert via the speakers 256 of the base unit 120 and/or via the speaker 268 of the wireless tag 115. In some embodiments, the system 100 can interface with multiple wireless scanners (e.g., Bluetooth scanners) strategically placed within a room or building to detect if the probes 110 are removed from the room or building.

The current method for detecting and locating nearby transducer probes requires that the operator of the ultrasound system look around and physically locate a desired transducer probe. The challenge of finding the transducer probe can be significant if the transducer probe is inside a drawer or otherwise out of sight—adding significant delay to an ultrasound imaging procedure. Accordingly, in contrast to conventional ultrasound systems, the present technology advantageously allows the operator of an ultrasound system to quickly view and/or locate nearby transducer probes. In addition, the present technology allows probes to be managed independently from a CPU system.

III. Selected Embodiments of Methods for Displaying, Filtering, and Sorting Proximate Transducer Probes With reference to FIG. 1, in some embodiments, the base unit 120 is configured to display a graphic on the display 122 showing the probes 110 that have been detected by the base unit 120 so that the operator of the system is informed of what probes 110 are nearby. The graphic can be any visual indication identifying the nearby probes 110 such as, for example, a list of serial numbers, images, physical characteristics, or other attributes of the probes 110. In some embodiments, the base unit 120 can further display all or a portion of the supplemental data received from the wireless tags 115 associated with the nearby probes 110. For example, the displayed graphic can include separate columns each identifying a different portion of the supplemental data associated with the nearby probes 110 (e.g., cleaning history, maintenance schedules, etc.). The displayed graphic could also include other indications based on the supplemental data—such as triangles with exclamation marks to distinguish the nearby probes 110 that need attention for maintenance or cleaning.

In some embodiments, the displayed graphic data can be manually or automatically sorted, filtered, augmented, etc., based on (i) the supplemental data received from the wireless tags 115 and/or (ii) an operator or other input to the system 100. In particular, the data in the graphic can be updated or modified to distinguish certain ones of the nearby probes 110 using, for example, color coding, ranking (e.g., placing certain probes 110 at the top of a displayed list), list trimming (e.g., removing certain probes 110 from a displayed list), or any other suitable method or combination thereof for prioritizing, distinguishing, and/or emphasizing certain ones of the probes 110 on the display 122.

In certain embodiments, for example, the operator of the system 100 can filter or sort the display of nearby probes 110 by manually entering information (e.g., a specific probe attribute) via the operator controls 124, and the base unit 120 can update, modify, etc., the data in the graphic on the display 122 to show the nearby probes 110 that have that attribute. For example, an ultrasound technician responsible for maintenance of the system 100 may want to filter the display of nearby probes 110 to show those that require maintenance or cleaning, while a sonographer may want to filter the display of nearby probes 110 to show those that have specific physical characteristics appropriate for an imaging procedure to be carried out by the sonographer. In either instance, the relevant probes 110 could be displayed alone, displayed at the top of a list, displayed in a certain color, etc., in order to distinguish the probes 110 having the specified attribute to the ultrasound technician/sonographer.

In some embodiments, the current operator of the system 100 may enter their identity (e.g., ultrasound technician, sonographer, etc.) and the display of nearby probes 110 may be updated to distinguish those nearby probes 110 that may be more pertinent to the current operator. For example, those proximate probes 110 that need maintenance or cleaning may be more pertinent to the ultrasound technician, while the opposite is likely true for a sonographer seeking a probe for a current imaging procedure. In yet another example, the supplemental data may include information about sonographers' preferred probes 110 (e.g., historical usage information), and the system 100 can display and/or distinguish those probes 110 after determining the identity of the sonographer using the system 100.

In some embodiments, the current operator may not be familiar with the exam room and location of probes. The operator may display a list of all probes available for use which may include drawer location, license information, owner, cost for use, performance capabilities, system compatibility, etc. For example, if the probes are managed by a third party, newer or more capable probes (e.g. those having fewer dead elements, increased element count, lower loss, etc.) may be presented and cost the operator more for usage.

In some embodiments, the display of nearby probes 110 may be updated to distinguish at least one appropriate (e.g., suitable, preferred, etc.) or more appropriate one of the proximate probes 110 for an imaging procedure to be carried out on the patient 1. FIG. 3, for example, is a flow diagram of a process or method 300 of selecting a nearby probe for an ultrasound imaging procedure using the system 100 in accordance with embodiments of the present technology.

Beginning at block 302, the method 300 includes detecting the probes 110 that are located proximate to the base unit 120 and receiving supplemental data from the wireless tags 115 associated with the nearby probes 110, as described in detail above. At block 304, the method includes receiving information about the imaging procedure and/or information about the patient 1. In some embodiments, for example, the operator (e.g., the sonographer) can use the operator controls 124 of the base unit 120 to enter or select information about the particular region of interest to be imaged, a particular feature to be imaged, the size/weight/height/age or other characteristic of the patient 1, etc. In a particular example, the operator of the system 100 could specify that the imaging procedure is a peripheral vascular examination and that the targeted structure is a varicose vein located near the skin surface of the patient 1.

At block 306, the method 300 includes determining which, if any, of the nearby probes 110 are appropriate for the specific imaging procedure and patient. In some embodiments, the determination can be based at least in part on predetermined rules and/or historical data about probes used in previous imaging procedures and on patients having certain characteristics. The predetermined rules and historical data can be stored in the memory of the base unit 120 or otherwise made accessible to the base unit 120. Continuing the particular example set forth above, the base unit 120 may determine that probes 110 having a higher frequency (e.g., 7.5 MHz) as opposed to a lower frequency (e.g., 5 MHz) are more appropriate for the peripheral vascular examination because the targeted varicose vein is located near the surface and thus the ultrasound waves need not penetrate as deeply and the resolution needed to find the vein is better with a high frequency probe.

As further examples of the determination at block 306, the base unit 120 can determine that a probe 110 having a curved transducer array that operates between 1-5 MHz is most appropriate for imaging procedures that are abdominal, spinal, pulmonary, gynecological, musculoskeletal, and/or obstetric examinations. Further, in some embodiments, the base unit 120 can determine that a probe 110 having a linear transducer array that operates between 3-12 MHz is most appropriate for imaging procedures that are superficial, breast, arterial, venous, and/or ophthalmic examinations. Likewise, in certain embodiments, the base unit 120 can determine that a probe 110 having a phased transducer array that operates between 1-5 MHz is most appropriate for imaging procedures that are neurovascular examinations.

At block 308, the method 300 includes displaying a graphic of the appropriate nearby probes 110 on the display 122. As set forth in detail above, the graphic can suitably distinguish (e.g., via color coding, ranking, etc.) the appropriate nearby probes 110 from the inappropriate or less appropriate nearby probes 110, or can list only the appropriate nearby probes 110. For example, the appropriate nearby probes 110 could be displayed at the top of a list of all nearby probes. In some embodiments, the method 300 may return to block 304 as the operator enters additional information about the patient 1 and/or the current imaging procedure. The method 300 can then proceed again through blocks 306 and 308 to further update the display of appropriate nearby probes 110. For example, the method 300 may proceed until only a single nearby probe 110 is displayed. If no appropriate probes 110 are detected, the graphic can include an indication that no appropriate probes 110 are nearby and, in some embodiments, can provide an indication of a determined next-best nearby probe 110 and/or an indication instructing the operator to search for nearby probes 110 in a different location (e.g., by moving the base unit 120 to another examination room in a medical facility).

In some embodiments, the system 100 can be configured to detect that one or more of the probes 110 are connected to the base unit 120 (e.g., via corresponding ones of the signal cables 130). Accordingly, the method 300 can further include determining whether the one or more connected probes 110 include the appropriate probes 110 as determined at block 306. If the determined appropriate probe 110 is not connected to the base unit 120, the method 300 can further include providing an indication or alert on the display 122 that the appropriate probe 110 is nearby but is not currently connected to the base unit 120. That is, the system 100 may prompt the operator to connect a different one of the nearby probes 110.

Some ultrasound imaging procedures are advantageously performed using two or more different probes (e.g., having different physical characteristics). Accordingly, in some embodiments, the method 300 can include determining two or more appropriate probes 110 based on received or selected information about the imaging procedure and/or the patient 1. In such embodiments, at block 308, the method 300 can include displaying the two or more appropriate probes 110 ordered or otherwise distinguished, for example, based on their presumptive order of use during the imaging procedure. Where the base unit 120 can be connected to two more of the probes 110, the display of nearby probes 110 can further include an indication of a particular I/O port 126 in which each of the appropriate probes 110 should be connected.

Current ultrasound systems rely on the experience of the operator and the records of the facility housing the ultrasound system to guide the operator in selecting a particular probe for a particular examination or for cleaning, maintenance, etc. In particular, it may be difficult for ultrasound technicians to reliably locate probes that need service, and sonographers may often select an inappropriate or less appropriate probe for a procedure than what is available nearby. Accordingly, in contrast to conventional ultrasound systems, the present technology advantageously permits operators to search for nearby probes having particular attributes of interest and can also guide operators in the selection of the most appropriate available probe.

IV. CONCLUSION

Embodiments of the subject matter and the operations described in this specification can be implemented in digital electronic circuitry, or in computer software, firmware, or hardware, including the structures disclosed in this specification and their structural equivalents, or in combinations of one or more of them. Embodiments of the subject matter described in this specification can be implemented as one or more computer programs, i.e., one or more modules of computer program instructions, encoded on computer storage medium for execution by, or to control the operation of, data processing apparatus.

A computer storage medium can be, or can be included in, a computer-readable storage device, a computer-readable storage substrate, a random or serial access memory array or device, or a combination of one or more of them. Moreover, while a computer storage medium is not a propagated signal, a computer storage medium can be a source or destination of computer program instructions encoded in an artificially-generated propagated signal. The computer storage medium also can be, or can be included in, one or more separate physical components or media (e.g., multiple CDs, disks, or other storage devices). The operations described in this specification can be implemented as operations performed by a data processing apparatus on data stored on one or more computer-readable storage devices or received from other sources.

The term "processor" encompasses all kinds of apparatus, devices, and machines for processing data, including by way of example a programmable processor, a computer, a system on a chip, or multiple ones, or combinations, of the foregoing. The apparatus can include special purpose logic circuitry, e.g., an FPGA (field programmable gate array) or an ASIC (application-specific integrated circuit). The apparatus also can include, in addition to hardware, code that creates an execution environment for the computer program in question, e.g., code that constitutes processor firmware, a protocol stack, a database management system, an operating system, a cross-platform runtime environment, a virtual machine, or a combination of one or more of them. The apparatus and execution environment can realize various different computing model infrastructures, such as web services, distributed computing and grid computing infrastructures.

A computer program (also known as a program, software, software application, script, or code) can be written in any form of programming language, including compiled or interpreted languages, declarative or procedural languages, and it can be deployed in any form, including as a stand-alone program or as a module, component, subroutine, object, or other unit suitable for use in a computing environment. A computer program may, but need not, correspond to a file in a file system. A program can be stored in a portion of a file that holds other programs or data (e.g., one or more scripts stored in a markup language document), in a single file dedicated to the program in question, or in multiple coordinated files (e.g., files that store one or more modules, sub-programs, or portions of code). A computer program can be deployed to be executed on one computer or on multiple computers that are located at one site or distributed across multiple sites and interconnected by a communication network.

The processes and logic flows described in this specification can be performed by one or more programmable processors executing one or more computer programs to perform actions by operating on input data and generating output. The processes and logic flows can also be performed by, and apparatus can also be implemented as, special purpose logic circuitry, e.g., an FPGA (field programmable gate array) or an ASIC (application-specific integrated circuit).

Generally, a processor will receive instructions and data from a read-only memory or a random access memory or both. The essential elements of a computer are a processor for performing actions in accordance with instructions and one or more memory devices for storing instructions and data. To provide for interaction with a user, embodiments of the subject matter described in this specification can be implemented on a imaging system having a display device, e.g., an LCD (liquid crystal display), LED (light emitting diode), or OLED (organic light emitting diode) monitor, for displaying information to the operator and a keyboard and a pointing device, e.g., a mouse or a trackball, by which the operator can provide input to the computer. In some implementations, a touch screen can be used to display information and to receive input from a user. Other kinds of devices can be used to provide for interaction with an operator as well; for example, feedback provided to the operator can be any form of sensory feedback, e.g., visual feedback, auditory feedback, or tactile feedback; and input from the operator can be received in any form, including acoustic, speech, or tactile input.

From the foregoing, it will be appreciated that specific embodiments of the technology have been described herein for purposes of illustration, but that various modifications may be made without deviating from the disclosure. Accordingly, the invention is not limited except as by the appended claims. Furthermore, certain aspects of the new technology described in the context of particular embodiments may also be combined or eliminated in other embodiments. Moreover, although advantages associated with certain embodiments of the new technology have been described in the context of those embodiments, other embodiments may also exhibit such advantages and not all embodiments need necessarily exhibit such advantages to fall within the scope of the technology. Accordingly, the disclosure and associated technology can encompass other embodiments not expressly shown or described herein.

We claim:

1. An ultrasound system, comprising:
   transducer probes having wireless tags configured to store transducer probe data about the transducer probes; and
   a base unit including a memory storing instructions and a processor configured to execute the instructions to cause the processor to:
   receive the transducer probe data from the wireless tags;
   receive ultrasound procedure data about a current ultrasound procedure for the ultrasound system; and
   select one transducer probe of the transducer probes for the current ultrasound procedure based on the transducer probe data and the ultrasound procedure data.

2. The ultrasound system of claim 1 wherein the processor is configured to execute the instructions to cause the processor to produce an indication that the one transducer probe is to be used for the current ultrasound procedure.

3. The ultrasound system of claim 1 wherein the processor is configured to execute the instructions to cause the processor to update the transducer probe data in one or more of the wireless tags in one or more of the transducer probes.

4. The ultrasound system of claim 1 wherein the processor is configured to execute the instructions to cause the processor to perform a search with respect to the transducer probes.

5. The ultrasound system of claim 4 wherein the search is to identify one or more of the transducer probes located within a predetermined range of the base unit.

6. The ultrasound system of claim 4 wherein the search is to identify one or more of the transducer probes having a set of attributes based on one or more of operator-entered information and information obtained from the wireless tags.

7. The ultrasound system of claim 1 wherein the processor is configured to cause an alert to indicate one or more of the transducer probes are out of range of the base unit.

8. The ultrasound system of claim 1 further comprising a display coupled to the base unit, wherein the processor is configured to execute the instructions to cause the processor to generate transducer probe information on the display based on a current operator identity for the system.

9. The ultrasound system of claim 8 wherein the transducer probe information comprises one or more of information indicating one or more transducer probes based on current operator proximity to the one or more transducer probes, one or more operator-preferred transducer probes, and one or more transducer probes based on the current operator identity.

10. A method for use by an ultrasound system having transducer probes and a base unit with a processor, the method comprising:
    receiving, by the processor, transducer probe data from wireless tags of the transducer probes;
    receiving, by the processor, ultrasound procedure data about a current ultrasound procedure for the ultrasound system; and
    selecting, by the processor, one transducer probe of the transducer probes for the current ultrasound procedure based on the transducer probe data and the ultrasound procedure data.

11. The method of claim 10 further comprising producing an indication that the one transducer probe is to be used for the current ultrasound procedure.

12. The method of claim 10 further comprising updating the transducer probe data in one or more of the wireless tags in one or more of the transducer probes.

13. The method of claim 10 further comprising performing a search with respect to the transducer probes.

14. The method of claim 13 wherein the search is to identify one or more of the transducer probes located within a predetermined range of the base unit.

15. The method of claim 13 wherein the search is to identify one or more of the transducer probes having a set of attributes based on one or more of operator-entered information and information obtained from the wireless tags.

16. The method of claim 10 further comprising generating an alert to indicate one or more of the transducer probes are out of range of the base unit.

17. The method of claim 10 further comprising selecting, based on a current operator identity, and displaying transducer probe information on a display of the ultrasound system.

18. The method of claim 17 wherein the transducer probe information comprises one or more of information indicating one or more transducer probes based on current operator proximity to the one or more transducer probes, one or more operator-preferred transducer probes, and one or more transducer probes based on the current operator identity.

19. An ultrasound system, comprising:
    transducer probes having wireless tags configured to store transducer probe data about the transducer probes; and
    a base unit including a memory storing instructions and a processor configured to execute the instructions to cause the processor to:
        receive the transducer probe data from the wireless tags;
        determine that at least one transducer probe of the transducer probes is located within a predetermined range of the base unit; and
        produce an indication of the at least one transducer probe.

20. The ultrasound system of claim 19 wherein the processor is configured to execute the instructions to cause the processor to determine the at least one transducer probe based on a current ultrasound procedure and patient data.

* * * * *